United States Patent [19]

Hirsch et al.

[11] Patent Number: 4,769,378

[45] Date of Patent: Sep. 6, 1988

[54] INDENOPYRIMIDINE AROMATASE INHIBITORS

[75] Inventors: Kenneth S. Hirsch; C. David Jones; Eriks V. Krumkalns, all of Indianapolis; Donald G. Saunders, Greenfield, all of Ind.

[73] Assignee: Eli Lilly and Company, Indianapolis, Ind.

[21] Appl. No.: 846,541

[22] Filed: Mar. 31, 1986

[51] Int. Cl.$^4$ ................ A61K 31/505; C07D 239/70
[52] U.S. Cl. .................................... 514/267; 544/249
[58] Field of Search ........................ 544/249; 514/267

[56] References Cited

U.S. PATENT DOCUMENTS

| | | | |
|---|---|---|---|
| 3,133,922 | 5/1964 | Vanhoof | 544/249 |
| 3,170,924 | 2/1965 | Vanhoof | 544/249 X |
| 3,177,216 | 4/1965 | Wagner | 544/249 X |
| 3,920,655 | 11/1975 | Rufer et al. | 544/298 X |
| 3,925,384 | 12/1975 | Krapcho et al. | 544/249 |
| 4,235,893 | 11/1980 | Brodie et al. | 260/397.4 X |

FOREIGN PATENT DOCUMENTS 116431  8/1984  European Pat. Off. .

OTHER PUBLICATIONS

Siiteri et al., *Handbok of Phisiology-Endocinology II,* Part I, Chapter 28, pp. 615–629.
Harris, Expl. Cell Biol., vol. 53, pp. 1–8 (1985).
Brodie et al., Endocrinology, vol. 100, pp. 1684–1695 (1977).
Goodman and Gilman's, "The Pharmacological Basis of Therapeutics", 6th ed., MacMillan Publishing Co., New York, p. 1034.
Coombes et al., Lancet, 12/01/84, pp. 1237–1239.
Santen et al., Anals of Internal Medicine, vol. 96, pp. 94–101 (1982).
Barone et al., J. Clinical Endocrinology and Metabolism, vol. 49, No. 5, pp. 672–676 (1979).
Cancer Research, vol. 42, No. 8, supplement, 8/82, "Conference on Aromatase: New Perspectives for Breast Cancer", Table of Contents, pp. 3263s–3266s.
Tseng et al., Obstetrics and Gynecology, vol. 63, No. 2, pp. 150–154 (2/84).
Berkowitz et al., Am. J. Epidemology, vol. 121, No. 2, pp. 238–245 (1985).
Tseng et al., J. Clinical Endocrinology and Medicine, vol. 55, No. 5, pp. 1029–1031 (1982).
Sedova, Chemical Abstracts, vol. 73, 77181z (1970).
Campaigne et al., *J. Het. Chem.,* 7 (4), 937–940 (1970).
Gilchrist et al., *J.C.S. Perkin I,* 1871–1878 (1979).
Toothill, *Dissertation Abstracts,* 25 (6), 3276 (1964).

*Primary Examiner*—Donald G. Daus
*Assistant Examiner*—Diana G. Rivers
*Attorney, Agent, or Firm*—Joseph A. Jones; Leroy Whitaker

[57] ABSTRACT

Certain 5-phenyl-5H-indeno[1,2-d]pyrimidines, their pharmaceutical formulations, and their use in methods for inhibiting aromatase and treating or preventing estrogen-dependent diseases.

20 Claims, No Drawings

INDENOPYRIMIDINE AROMATASE INHIBITORS

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research*, Vol. 42, Suppl 8, especially page 3261s et seq. (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer*, 25, 270 (1971)). Two of the known aromatase inhibitors, testololactone and aminoglutethimide, have shown a beneficial effect in treatment of breast cancer. See *Cancer Research*, supra.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer*, 49, 2534 (1982). Aromatase inhibitors have not been tried in this disease, but antiestrogens seem to be of benefit. See *Obstet. Gynecol*, 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.*, 12, 177 (1980).

It is the purpose of this invention to provide compounds which inhibit the enzyme aromatase in mammals and are therefore useful in the treatment or prevention of breast cancer and other estrogen-dependent diseases.

SUMMARY OF THE INVENTION

This invention provides indenopyrimidines of the formula I

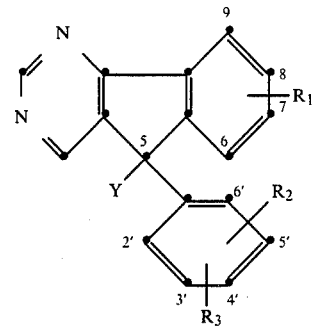

wherein
Y is hydrogen, hydroxy, chloro, fluoro, or —NHCOCH$_3$; R$_1$ is hydrogen, chloro, fluoro, methoxy, or trifluoromethyl; and
each of R$_2$ and R$_3$ is independently hydrogen, chloro, fluoro, or trifluoromethyl.

This invention also provides a method of inhibiting aromatase in mammals which comprises the administration of an aromatase inhibiting amount of a compound of this invention. By virtue of their ability to inhibit the enzyme aromatase, the compounds of formula I are useful in the treatment and prevention of estrogen-dependent diseases, especially breast cancer, in mammals.

A further aspect of this invention is a pharmaceutical formulation comprising an effective amount of a compound of this invention in combination with a suitable pharmaceutical carrier, diluent, or excipient therefor. The formulations provided by this invention are particularly useful in treating mammals suffering from estrogen-dependent diseases such as breast cancer.

DETAILED DESCRIPTION AND PREFERRED EMBODIMENT

A preferred group of compounds useful in this invention are the compounds of formula I wherein:
(a) Y is hydroxy or especially hydrogen,
(b) R$_1$ is chloro or fluoro, especially at the 8-position,
(c) one of R$_2$ and R$_3$ is hydrogen, and
(d) the other of R$_2$ and R$_3$ is chloro or fluoro, especially in the 4'-position.

A preferred method of treatment according to this invention comprises administering a dose effective for inhibiting the enzyme aromatase of one of the preferred compounds of this invention. Similarly, a preferred formulation according to this invention comprises one of the preferred compounds of this invention in combination with a pharmaceutical carrier therefor.

The compounds of this invention may be prepared according to general procedures known in the art as summarized in the following scheme:

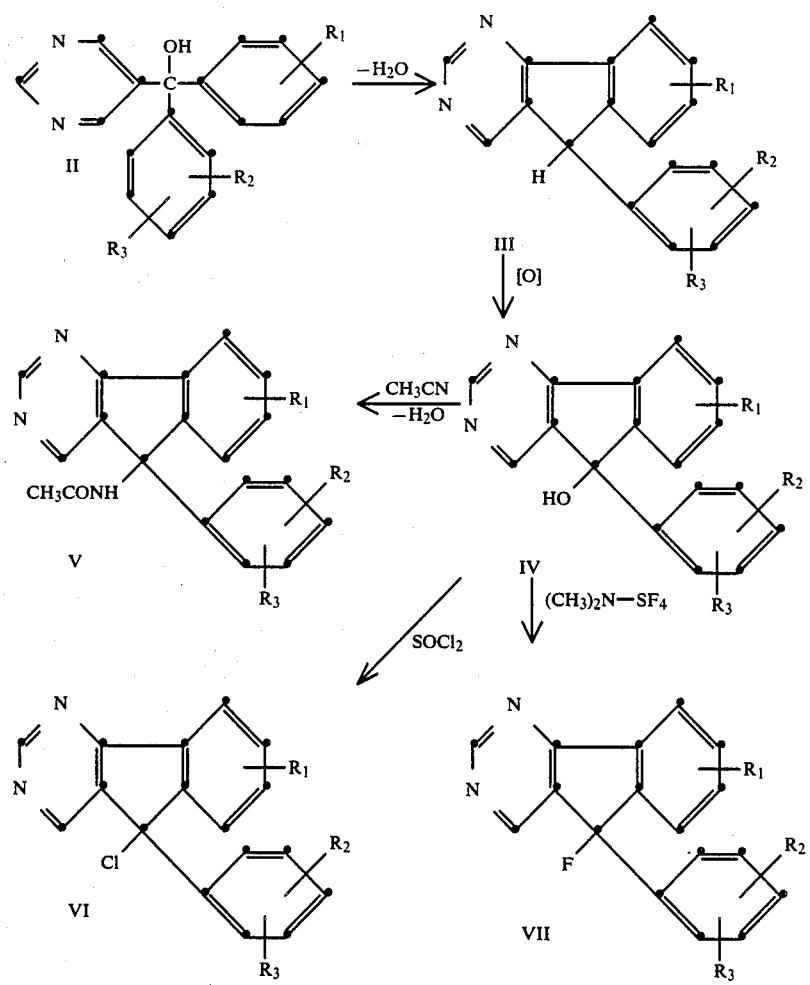

The compounds of this invention wherein Y is hydrogen (Formula III) may be prepared from the corresponding α,α-diphenyl-5-pyrimidinemethanols II by dehydration. This reaction may, depending upon the definitions of the various R substituents, provide two or more different indenopyrimidines of Formula III which may be separated by known methods such as fractional crystallization or chromatography.

The dehydration of II is accomplished by any of several general methods known in the art. For example, a preferred method comprises stirring a solution of the pyrimidinemethanol II in methanesulfonic acid. Typically, temperatures of 20°-30° C. are employed and the reaction is complete within 12-24 hours. The reaction is preferably carried out under an inert atmosphere. Alternatively, concentrated sulfuric acid may be employed in place of the methanesulfonic acid.

The indenopyrimidines of formula III may be converted to the carbinols of formula IV by any of several oxidative procedures known in the art. For example, the oxidation may be accomplished by treating a compound of formula III with an oxidizing agent such as potassium permanganate in an inert solvent such as acetone under an inert atmosphere. The reaction is generally carried out at ambient temperature and is usually complete in 4-18 hours. Similarly, the oxidation may be accomplished by dissolving the indenopyrimidine III in dimethylsulfoxide, adding approximately 1 molar equivalent of a strong base, such as sodium hydroxide, and bubbling oxygen gas through the solution. This reaction provides a near quantitative conversion of III into IV and is generally complete in 2-4 hours when performed at ambient temperature.

The compounds of formula IV may be transformed into the acetamide derivatives of formula V by mixing the carbinol with acetonitrile and methanesulfonic acid. At temperatures from about 20°-30° C., the reaction is usually complete in 12-18 hours.

Chloro analogs VI may also be prepared from the carbinol IV upon treatment with thionyl chloride. This reaction is easily accomplished by stirring the carbinol and thionyl chloride for 2-4 hours at room temperature.

The analogous fluoro compounds VII are also prepared from the carbinol IV upon treatment with diethylaminosulfur trifluoride in a non-reactive solvent such as dichloromethane. This reaction is best accomplished when performed at about 0° C. and under inert atmosphere. Under these conditions, the reaction is generally complete within 4-18 hours.

The intermediates of formula II are disclosed in U.S. Pat. No. 3,818,009. A preferred and novel method of preparing such compounds is also taught in U.S. Pat. No. 3,869,456. Both patents are expressly incorporated in this application by reference. Other required intermediates may be prepared in analogous fashion. Other reagents required in the above transformations are commercially available or can be prepared by methods known in the art.

As will be recognized by those skilled in the art, the compounds of Formula I contain an asymmetric carbon atom. This invention is not limited to any particular isomer but includes the individual enantiomers as well as the racemates of the compounds of Formula I.

The following Examples further illustrate the preparation of the compounds of this invention. The examples are illustrative only and are not intended to limit the scope of the invention in any way.

EXAMPLE 1

8-chloro-5-(4-chlorophenyl)-5H-indeno[1,2-d]pyrimidine

A solution of 4.0 g of α, α-bis(4-chlorophenyl)-5-pyrimidinemethanol in 25 ml of methanesulfonic acid was stirred under a nitrogen atmosphere for 18 hours. The solution was poured into a sodium bicarbonate solution and extracted with ethyl acetate. The organic extract was washed with a saturated sodium chloride solution, dried over magnesium sulfate, and concentrated in vacuo. Recrystallization from ethyl acetate/isooctane provided 1.95 g of the desired title product, m.p. 158°–163° C.

Analysis for $C_{17}H_{10}Cl_2N_2$
Calculated: C, 65.20; H, 3.22; N, 8.94;
Found: C, 65.03; H, 3.29; N, 8.73.

EXAMPLES 2–6

The following compounds were prepared from the corresponding pyrimidinemethanol according to the procedure of Example 1.

2. 5-(4-chlorophenyl)-5H-indeno[1,2-d]pyrimidine, 73% yield, m.p. 140°–140.5° C.
Analysis for $C_{17}H_{11}ClN_2$
Calculated: C, 73.25; H, 3.98; N, 10.05;
Found: C, 73.29; H, 3.72; N, 9.87.

3. 8-chloro-5-phenyl-5H-indeno[1,2-d]pyrimidine, 0.3% yield, m.p. 135.5°–137° C.
Analysis for $C_{17}H_{11}ClN_2$
Calculated: C, 73.25; H, 3.98; N, 10:05;
Found: C, 72.19; H, 3.81; N, 9.87.

4. 5-(4-fluorophenyl)-8-(trifluoromethyl)-5H-indeno[1,2-d]pyrimidine, 0.8% yield, m.p. 146°–148° C.
Analysis for $C_{18}H_{10}F_4N_2$
Calculated: C, 65.46; H, 3.05; N, 8.48;
Found: C, 65.18; H, 3.11; N, 8.21.

5. 8-fluoro-5-[4-(trifluoromethyl)phenyl]-5H-indeno[1,2-d]pyrimidine, 33% yield, m.p. 169°–170° C.
Analysis for $C_{18}H_{10}F_4N_2$
Calculated: C, 65.46; H, 3.05; N, 8.48;
Found: C, 65.74; H, 3.23; N, 8.48.

6. 8-fluoro-5-(4-fluorophenyl)-5H-indeno[1,2-d]pyrimidine, 77.7% yield, m.p. 172°–174° C.
Analysis for $C_{17}H_{10}F_2N_2$
Calculated: C, 72.85; H 3.60; N, 10.00;
Found: C, 73.04; H, 3.87; N, 9.96.

EXAMPLE 7

5-phenyl-5H-indeno[1,2-d]pyrimidine

Ten grams of α, α-diphenyl-5-pyrimidinemethanol were stirred in 50 ml of sulfuric acid for approximately 18 hours. The solution was poured onto ice and the resulting solids were recovered by filtration providing 11 g of the desired title product. Recrystallization from diethyl ether provided material with a melting point of 148°–150° C.

Analysis for $C_{17}H_{12}N_2$
Calculated: C, 83.58; H, 4.95; N, 11.49;
Found: C, 83.33; H, 5.17; N, 11.11.

EXAMPLES 8–17

The following compounds were prepared from the corresponding pyrimidinemethanol according to the procedure of Example 7.

8. 5-(2,4-dichlorophenyl)-5H-indeno[1,2-d]pyrimidine, 80% yield, m.p. 107°–108° C.

9. 5-(3-fluorophenyl)-5H-indeno[1,2-d]pyrimidine, 21% yield, m.p. 121° C. The proton NMR spectra was consistent with the structure of the desired product.

10. 5-(2,5-dichlorophenyl)-5H-indeno[1,2-d]pyrimidine, m.p. 145° C.
Analysis for $C_{17}H_{10}Cl_2N_2$
Calculated: C, 65.20; H, 3.22; N, 8.94;
Found: C, 65.31; H, 3.22; N, 9.07.

11. 5-(3,4-dichlorophenyl)-5H-indeno[1,2-d]pyrimidine, 42% yield, m.p. 151° C.
Analysis for $C_{17}H_{10}Cl_2N_2$
Calculated: C, 65.20; H, 3.22; N, 8.94;
Found: C, 65.29; H, 3.25; N, 8.66.

12. 5-(4-chlorophenyl)-7-methoxy-5H-indeno[1,2-d]pyrimidine, 58% yield, m.p. 164° C.
Analysis for $C_{18}H_{13}ClN_2O$
Calculated: C, 70.02; H, 4.24; N, 9.07;
Found: C, 69.85; H, 4.50; N, 8.84.

13. 5-(4-fluorophenyl)-7-methoxy-5H-indeno[1,2-d]pyrimidine, 74% yield.
Analysis for $C_{18}H_{13}FN_2O$
Calculated: C, 73.96; H, 4.48; N, 9.58;
Found: C, 73.70; H, 4.44; N, 9.51.

14. 5-(2-fluorophenyl)-5H-indeno[1,2-d]pyrimidine, 67% yield, m.p. 124°–125° C.
Analysis for $C_{17}H_{11}FN_2$
Calculated: C, 77.83; H, 4.23; N, 10.68;
Found: C, 77.95; H, 4.32; N, 10.82.

15. 5-(4-fluorophenyl)-5H-indeno[1,2-d]pyrimidine, 87% yield, m.p. 128° C. The proton NMR spectrum was consistent with the structure of the desired product.

16. 5-(3-chlorophenyl)-8-methoxy-5H-indeno[1,2-d]pyrimidine, 2.6% yield, m.p. 147° C.
Analysis for $C_{18}H_{13}ClN_2O$
Calculated: C, 70.02; H, 4.24; N, 9.07;
Found: C, 69.74; H, 3.95; N, 8.85.

17. 7-fluoro-5-(2-fluorophenyl)-5H-indeno[1,2-d]pyrimidine, m.p. 143°–145° C.
Analysis for $C_{17}H_{10}F_2N_2$
Calculated: C, 72.85; H, 3.60; N, 10.00;
Found: C, 72.64; H, 3.90; N, 9.75.

EXAMPLE 18

8-chloro-5-(4-chlorophenyl)-5H-indeno[1,2-d]pyrimidin-5-ol

To a stirred solution of 11.0 g of 8-chloro-5-(4-chlorophenyl)-5H-indeno[1,2-d]pyrimidine in 300 ml of acetone were added 6.32 g of potassium permanganate. The mixture was stirred under a nitrogen atmosphere for 2 hours at which time an additional 6.32 g of potassium permanganate were added. The mixture was stirred overnight at room temperature, filtered, and the filtrate concentrated in vacuo. The residue was taken up in a mixture of ethyl acetate and a saturated sodium chloride solution. The layers were separated and the organic layer was washed with water, dried over magnesium sulfate, filtered and concentrated in vacuo. The residue was crystallized first from ethyl acetate/isooctane and then from ethyl acetate to provide 3.06 g of the desired title product, m.p. 194°–195.5° C.

Analysis for $C_{17}H_{10}Cl_2N_2O$
Calculated: C, 62.03; H, 3.06; N, 8.51; Cl; 21.54;
Found: C, 62.12; H, 3.35; N, 8.39; Cl; 21.58.

EXAMPLE 19

2-(2,4-dichlorophenyl)-5H-indeno[1,2-d]pyrimidin-5-ol

A mixture of 14.0 g of 5-(2,4-dichlorophenyl)-5H-indeno[1,2-d]pyrimidine and 2 g of powdered sodium hydroxide in 100 ml of dimethylsulfoxide was treated with oxygen gas introduced through a glass frit addition tube beneath the surface of the solution. The mixture was stirred for 1 hour, poured into cold water, and adjusted to pH 7 with hydrochloric acid. The resulting solid was recovered by filtration, washed with water, and dried to provide 10 g of the desired title product, m.p. 188° C.

Analysis for $C_{17}H_{10}Cl_2N_2O$
Calculated: C, 62.03; H, 3.06; N, 8.51;
Found: C, 61.73; H, 3.23; N, 8.24.

EXAMPLE 20–22

The following compounds were prepared from the corresponding indenopyrimidines according to the procedure of Example 19.

20. 5-(4-chlorophenyl)-7-methoxy-5H-indeno[1,2-d]pyrimidin-5-ol, 78% yield, m.p. 84° C.
Analysis for $C_{18}H_{13}ClN_2O_2$
Calculated: C, 66.57: H, 4.03; N, 8.63;
Found: C, 66.59; H, 4.26; N, 8.43.

21. 5-(4-fluorophenyl)-5H-indeno[1,2-d]pyrimidin-5-ol, 84.5% yield, m.p. 195° C.
Analysis for $C_{17}H_{11}FN_2O$
Calculated: C, 73.37; H, 3.98; N, 10.07;
Found: C, 73.14; H, 4.05; N, 9.96.

22. 8-chloro-5-(2-chlorophenyl)-5H-indeno[1,2-d]pyrimidin-5-ol, 17% yield, m.p. 178°–179° C.
Analysis for $C_{17}H_{10}Cl_2N_2O$
Calculated: C, 62.03; H, 3.06; N, 8.51;
Found: C, 61.82; H, 3.00; N, 8.71.

EXAMPLE 23

N-[8-chloro-5-(4-chlorophenyl)-5H-indeno[1,2-d]pyrimidin-5-yl]acetamide

A mixture of 3.0 g of 8-chloro-5-(4-chlorophenyl)-5H-indeno[1,2-d]pyrimidin-5-ol in 15 ml of acetonitrile and 50 ml of methanesulfonic acid were stirred for approximately 18 hours. The reaction mixture was added to a large excess of a potassium bicarbonate solution and the resulting mixture was extracted with ethyl acetate. The organic layer was washed with a saturated sodium chloride solution, dried over magnesium sulfate, and concentrated in vacuo. Crystallization from acetonitrile/water provided 2.53 g of the desired title product, m.p. 238°–241° C. Two further recrystallizations provided material with a melting point of 245°–248° C.

Analysis for $C_{19}H_{13}Cl_2N_3O$
Calculated: C, 61.64; H, 3.54; N, 11.35;
Found: C, 61.91; H, 3.71; N, 11.28;

EXAMPLES 24–25

The following compounds were prepared from the corresponding indenopyrimidin-5-ol according to the procedure of Example 23.

24. N-[5-(4-fluorophenyl)-5H-indeno[1,2-d]pyrimidin-5-yl]acetamide, m.p. 244° C.
Analysis for $C_{19}H_{14}FN_3O$
Calculated: C, 71.46; H, 4.42; N, 13.16;
Found: C, 71.67; H, 4.45; N, 12.90.

25. N-[5-(2,4-dichlorophenyl)-5H-indeno[1,2-d]pyrimidin-5-yl]acetamide, 62% yield, m.p. 290° C.
Analysis for $C_{19}H_{13}Cl_2N_3O$
Calculated: C, 61.64; H. 3.54: N, 11.35;
Found: C, 61.82; H, 3.55; N, 11.36.

EXAMPLE 26

5-chloro-5-phenyl-5H-indeno[1,2-d]pyrimidine

Five grams of 5-phenyl-5H-indeno[1,2-d]pyrimidin-5-ol were stirred at reflux temperature in 25 ml of thionyl chloride and 100 ml of benzene for 5 hours. The solvents were removed by evaporation and the residue was tritrated with benzene and filtered. The solid was crystallized from diethyl ether to provide 3 g of the desired title product, m.p. 119°–120° C.

Analysis for $C_{17}H_{11}ClN_2$
Calculated: C, 73.25; H, 3.98; N, 10.05;
Found: C, 73.11; H, 4.12; N, 9.84.

EXAMPLE 27

5,8-dichloro-5-(4-chlorophenyl)-5H-indeno[1,2-d]pyrimidine

The title product was prepared from the corresponding carbinol in 70.5% yield according to the procedure of Example 26, m.p. 152°–153° C.

Analysis for $C_{17}H_9Cl_3N_2$
Calculated: C, 58.74; H, 2.61; N, 8.06;
Found: C, 58.51; H, 2.81; N, 8.02.

EXAMPLE 28

8-chloro-5-(4-chlorophenyl)-5-fluoro-5H-indeno[1,2-d]pyrimidine

A mixture of 3.0 g of 8-chloro-5-(4-chlorophenyl)-5H-indeno[1,2-d]pyrimidin-5-ol in 50 ml of methylene chloride was cooled to 0° C. under a nitrogen atmosphere. Approximately 2.7 g of diethylaminosulfur trifluoride were added and the reaction was stirred overnight. The mixture was poured into an iced solution of potassium bicarbonate and extracted with ethyl acetate. The organic extract was washed with a sodium bicarbonate solution and a sodium chloride solution, dried over magnesium sulfate, and concentrated in vacuo. Crystallization from ethyl acetate/isooctane provided 2.29 g of the desired title product, m.p. 236°–237° C.

Analysis for $C_{17}H_9Cl_2FN_2$
Calculated: C, 61.65; H, 2.74; N, 8.46;
Found: C, 61.88; H, 2.97; N, 8.58.

The compounds of this invention are useful in preventing or therapeutically treating estrogen-dependent diseases, including breast cancer, in mammals by virtue of their ability to inhibit the enzyme aromatase. The compounds have also been shown to be much less likely to induce an increase of hepatic microsomal enzymes such as cytochrome P-450. The ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 μM 4-androstene-3,17-dione, 100,000 dpm 1,2[$^3$H]-androstenedione, the microsomes and a NADPH generating system. The concentrations of the inhibitors tested ranged between 5 and 10000 nM. In this assay, aromatization of androstenedione results in the production of [$^3$H]-H$_2$O which is isolated by extracting the samples with chloroform and treating the aqueous phase with charcoal to remove the free steroid. Samples are counted in a liquid scintillation spectrometer and the percent inhibition determined by comparing the results with the samples incubated without inhibitor. Potency is determined based on the concentration of inhibitor in nM required to produce a 50% inhibition of enzyme activity (EC$_{50}$) when the concentration of substrate (androstenedione) is 0.1 μM. The EC$_{50}$'s of certain of the compounds of formula I are summarized in Table 1.

TABLE 1

Aromatase Inhibition in the Rat Ovarian Microsome Assay

| Compound of Example No. | EC$_{50}$* |
|---|---|
| 1 | 24 |
| 2 | 21 |
| 3 | 21 |
| 4 | 27 |
| 5 | 50 |
| 6 | 24 |
| 7 | 84 |
| 8 | 63 |
| 9 | <50 |
| 10 | 84 |
| 11 | <50 |
| 12 | 128 |
| 13 | 61 |
| 14 | 86 |
| 15 | <50 |
| 16 | <50 |
| 17 | 750 |
| 18 | 26 |
| 19 | 255 |
| 20 | 420 |
| 21 | <50 |
| 22 | 50 |
| 23 | 265 |
| 24 | 69 |
| 25 | 500 |
| 26 | 118 |
| Compound of Formula I | |
| 27 | 72 |
| 28 | 35 |

*Concentration of compound in nM required to achieve 50% inhibition of aromatase activity when substrate concentration is 0.1 μM.

By virtue of their ability to inhibit the enzyme aromatase, the compounds of this invention are able to inhibit the synthesis of estrogens in mammals, thereby making the compounds useful in the treatment of estrogen-dependent diseases, such as breast cancer. This in vivo activity was demonstrated in the following test systems.

Estrogen Synthesis Inhibition in Rats

Immature female Wistar rats (45-55 grams) were divided into control and test groups of 2-8 animals each. Test compounds were administered for seven days daily by gavage in corn oil. Control animals received corn oil without the test compound. Beginning on the fourth day of the test, all animals treated with the test compound and one half of the control animals were given a subcutaneous injection of 1.0 mg of testosterone propionate in corn oil. The remaining control animals received only an equivalent volume of corn oil. On the seventh day of the test, rats treated with testosterone propionate were injected subcutaneously with 100 μCi of [$^3$H]-testosterone in 50 μl of saline-ethanol (3:1).

After two hours, the animals were killed by decapitation. Uteri were isolated, trimmed of extraneous connective tissue, and weighed. The corn oil-treated animals exhibited low uterine weight and represent unstimulated or negative controls. In the control animals treated with testosterone propionate, estrogens produced by aromatization stimulated the uterus resulting in an increase in weight. Compounds which inhibit aromatization produced uterine weights significantly lower than those of the testosterone treated controls.

Ovaries from rats treated with [$^3$H]-testosterone were excised, cleaned of extraneous tissue, and homogenized in 2.5 ml of a 1.0 mM potassium phosphate buffer containing 3.0 mM MgCl$_2$.6H$_2$O, 320 mM sucrose, and 0.25% Triton X-100 (polyethylene glycol p-isooctyl phenyl ether, Rohm and Haas) at pH 6.5. The ovarian steroids were extracted with 1.5 ml of 9:1 toluene/ethanol to which had been added 25 to 100 mcg each of unlabelled estradiol, estriol, and estrone, and approximately 1000 dpm of [$^{14}$C]-estradiol. The samples were vortexed, centrifuged at 500×g for 10 minutes, and the organic phase was transferred to a conical vial. Two additional extractions were performed on the residue in the same way. The pooled organic extracts were evaporated for subsequent thin-layer chromatography.

Ovarian proteins were precipitated by the addition of 5.0 ml of ethanol to the remaining aqueous phase. After an overnight incubation at 4° C., the samples were centrifuged at 1500×g for 10 minutes. The supernatant was discarded and the pellet was dissolved in 0.3 N potassium hydroxide. Protein was determined according to the method of Bradford, *Analytical Biochemistry*, 72, 248 (1976).

The organic residue from each above extraction was redissolved in 9:1 dichloromethane/methanol. The solution of each sample was applied to separate silica gel thin layer chromatography plates which contained a fluorescent indicator. The plates were developed the first dimension with 160:38:1.5:0.5 dichloromethane/ethyl acetate/methanol/acetic acid to within 3 cm of the top of the plate. After air-drying, the plate was developed in the second dimension with 180:19:1 dichloromethane/methanol/ammonium hydroxide. The plate was air-dried and viewed under 254 nm UV light.

The visible spots were marked and the plates were sprayed with primulin (0.001% in 4:1 acetone/water) according to the method of Wright, *J. Chromatography*, 59, 220 (1971) which allowed for the identification of additional steroids under 365 nm UV light. The spots were scraped from the plate using a glass wool plugged Pasteur pipet attached to a vacuum line. The steroids were eluted directly into scintillation vials by the addition of 0.2 ml of dichloromethane followed by two washes each of 2.0 ml of methanol. The organic solvent was evaporated and 10.0 ml of scintillation fluid (Beckman Ready Solv-NA) was added to the vials. Samples were analyzed by liquid scintillation spectrometry and the corrections were made based on the recoveries of the [$^{14}$C]-steroid.

In Table 2, values for uterine weight are expressed as the respective weights of drug treated (DT), unstimulated corn oil control (UC), and stimulated corn oil control (SC) according to the calculation %=100 (DT-UC)/(SC-UC). Values for the estrogens are reported as the percent of values determined for testosterone-treated control animals.

TABLE 2

| Compound of Example No. | Dose* | Uterine Wt. %** | % steroid concentration*** | |
|---|---|---|---|---|
| | | | estradiol | estrone |
| 1 | 3 | 50.2+ | 31.5+ | 31.5 |
| | 10 | 37.3+ | 17.2+ | 31.4 |
| | 30 | 20.6+ | 23.6+ | 117.9 |
| 2 | 3 | 49.1+ | 40.5+ | 106.3 |
| | 30 | 33.3+ | 19.4+ | 83.2 |
| 4 | 3 | −14.3+ | samples | |
| | 30 | −35.5+ | contaminated | |
| 5 | 3 | 47.3+ | samples | |
| | 30 | 22.8+ | contaminated | |
| 6 | 3 | 0.7+ | 10.2+ | 70.3 |
| | 30 | 6.9+ | 2.9+ | 57.1+ |
| 18 | 3 | 30.4+ | 16.8+ | 89.0 |
| | 30 | −7.7+ | 7.5+ | 77.0+ |
| 19 | 3 | 69.6 | 78.3 | 115.7+ |
| | 30 | 42.8+ | 60.0 | 75.4 |
| 21 | 3 | 46.4+ | 14.5+ | 83.8 |
| | 30 | 17.9+ | 8.8+ | 71.3 |
| 22 | 3 | 70.0 | 79.4 | 73.4+ |
| | 30 | 57.4+ | 40.8+ | 90.1 |
| 24 | 3 | 32.3+ | 43.2+ | 71.9+ |
| | 30 | 23.2+ | 19.2+ | 59.9+ |

*mg/kg × 7 days
**% = 100 (DT-UC)/(SC-UC); see text
***percent of testosterone-treated controls
+significantly different from control $p < 0.05$ DMBA-induced Mammary Tumor Inhibition Mammary tumors were produced in female Sprague-Dawley rats which were 50–60 days old by the gavage administration of 20 mg of 7,12-dimethylbenz[a]anthracene (DMBA). About six weeks after DMBA administration, the mammary glands were palpated at weekly intervals for the appearance of tumors. Whenever one or more tumors appeared and were measurable in an animal, that animal was selected for experimentation. An attempt was made to uniformly distribute the various sizes of tumors in the treated and control groups such that one group did not start with rats having tumors which, on the average, were significantly larger than those of any other group. Each control and test group contained 5–8 animals. Each test compound was administered in corn oil once daily by gavage. Every experiment included a group of control rats having tumors and were given corn oil vehicle by gavage. The tumors were measured at the start of the experiments and generally had an area of approximately 15–100 mm². The area of each tumor was calculated by multiplying the shortest and longest diameters of the tumor. The treatment and measurement of animals continued for 4–6 weeks at which time the final areas of the tumors were determined. For each compound (and control) at each dose level, the change in the mean tumor area was determined. The mean change was analyzed for its significance using Dunnett's t-test. The results of these tests are shown in Table 3 below.

TABLE 3

| Test No. | Compound of Example | Anti-Tumor Activity | | Final Tumor Area (mm²) ± S.E. |
|---|---|---|---|---|
| | | Dose* | Duration of Test | |
| I | Control | — | 4 weeks | 741 ± 193 |
| | 1 | 3 | | 162 ± 93+ |
| | | 10 | | 74 ± 45+ |
| | | 30 | | 6 ± 6+ |
| II | Control | — | 4 weeks | 698 ± 78 |
| | 2 | 10 | | 287 ± 94 |
| | | 30 | | 814 ± 223 |
| | | 50 | | 552 ± 177 |
| III | Control | — | 6 weeks | 2053 ± 778 |
| | 6 | 10 | | 109 ± 62+ |
| | | 30 | | 393 ± 254 |

*mg/kg given daily by gavage.
+statistically different from control, $p < 0.05$.

In order to more fully illustrate the operation of this invention, the following formulation examples are provided. The examples are illustrative only and are not intended to limit the scope of the invention.

EXAMPLE 29

Hard gelatin capsules are prepared using the following ingredients:

| | per capsule |
|---|---|
| 8-chloro-5-(4-chlorophenyl)-5H—indeno[1,2-d]pyrimidine | 250 mg |
| Starch dried | 200 mg |
| Magnesium stearate | 10 mg |
| Total | 460 mg |

The above ingredients are mixed and filled into hard gelatin capsules in 460 mg quantities.

EXAMPLE 30

Capsules each containing 20 mg of medicament are made as follows:

| | per capsule |
|---|---|
| 8-fluoro-5-[4-(trifluoromethyl)phenyl]-5H—indeno-[1,2-d]pyrimidine | 20 mg |
| Starch | 89 mg |
| Microcrystalline cellulose | 89 mg |
| Magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

EXAMPLE 31

Capsules each containing 100 mg of active ingredient are made as follows:

| | per capsule |
|---|---|
| 5-phenyl-5H—indeno[1,2-d]-pyrimidine | 100 mg |
| Polyoxyethylenesorbitan monooleate | 50 mcg |
| Starch powder | 250 mg |

The above ingredients are thoroughly mixed and are placed in an empty gelatin capsule.

EXAMPLE 32

Tablets each containing 10 mg of active ingredient are made up as follows:

| | per tablet |
|---|---|
| 8-Chloro-5-(4-chlorophenyl)-5H—indeno[1,2-d]pyrimidin-5-ol | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 33

A tablet formula is prepared using the ingredients below:

| | per tablet |
|---|---|
| N—[5-(4-fluorophenyl)-5H—indeno-[1,2-d]pyrimidin-5-yl]acetamide | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 34

Suppositories each containing 25 mg of active ingredient are made as follows:

| | per suppository |
|---|---|
| 5,8-Difluoro-5-(2-chloro-4-fluorophenyl)-5H—indeno[1,2-d]-pyrimidine | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 35

Suspensions each containing 5 mg of medicament per 5 ml. dose are made as follows:

| | per 5 ml of suspension |
|---|---|
| 5-(4-trifluoromethylphenyl)-8-(trifluoromethyl)-5H—indeno[1,2-d]pyrimidine | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 36

An aerosol solution is prepared containing the following components:

| | Weight % |
|---|---|
| 5-(4-chlorophenyl)-8-methoxy-5H—indeno[1,2-d]pyrimidin-5-ol | 0.25 |
| Ethanol | 29.75 |
| Propellant 22 (Chlorodifluoromethane) | 70 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A compound of the formula

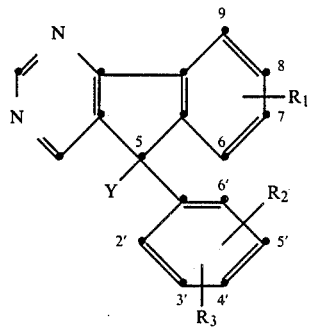

wherein
Y is hydrogen, hydroxy, chloro, fluoro, or —NHCOCH$_3$; R$_1$ is hydrogen, chloro, fluoro, methoxy, or trifluoromethyl; and
each of R$_2$ and R$_3$ is independently hydrogen, chloro, fluoro, or trifluoromethyl.

2. A compound of claim 1 wherein Y is hydrogen or hydroxy.

3. A compound of claim 2 wherein one of R$_2$ and R$_3$ is chloro or fluoro at the 4'-position.

4. A compound of claim 3 wherein R$_1$ is chloro or fluoro at the 8-position.

5. The compound of claim 4 which is 8-chloro-5-(4-chlorophenyl)-5H-indeno[1,2-d]pyrimidine.

6. The method of inhibiting aromatase in a mammal which comprises administering to said mammal an aromatase inhibiting amount of a compound of claim 1.

7. The method of claim 6 employing a compound wherein Y is hydrogen or hydroxy.

8. The method of claim 7 employing a compound wherein $R_1$ is chloro or fluoro at the 8-position and one of $R_2$ and $R_3$ is chloro or fluoro at the 4'-position.

9. The method of claim 8 employing 8-chloro-5-(4-chlorophenyl)-5H-indeno[1,2-d]pyrimidine.

10. The method of preventing or treating estrogen-dependent diseases in a mammal which comprises administering an effective amount of a compound of claim 1.

11. The method of claim 10 employing a compound wherein Y is hydrogen or hydroxy.

12. The method of claim 11 employing 8-chloro-5-(4-chlorophenyl)-5H-indeno[1,2-d]pyrimidine.

13. The method according to claim 10 wherein the estrogen-dependent disease is breast cancer.

14. The method of claim 13 employing a compound wherein Y is hydrogen or hydroxy.

15. The method of claim 14 employing 8-chloro-5-(4-chlorophenyl)-5H-indeno[1,2-d]pyrimidine.

16. A pharmaceutical formulation which comprises an effective amount of a compound of claim 1 in combination with suitable pharmaceutical carriers, diluents, or excipients therefor.

17. A formulation according to claim 16 employing a compound wherein Y is hydrogen or hydroxy.

18. A formulation according to claim 17 employing a compound wherein one of $R_2$ and $R_3$ is chloro or fluoro at the 4'-position.

19. A formulation according to claim 18 employing a compound wherein $R_1$ is chloro or fluoro at the 8-position.

20. A formulation according to claim 19 employing 8-chloro-5-(4-chlorophenyl)-5H-indeno[1,2-d]pyrimidine.

* * * * *